United States Patent
Damadian et al.

(10) Patent No.: US 11,406,276 B1
(45) Date of Patent: Aug. 9, 2022

(54) VISUALIZATION OF SPINAL ABNORMALITY USING UPRIGHT MR IMAGING DURING SPINAL TREATMENT

(71) Applicant: Fonar Corporation, Melville, NY (US)

(72) Inventors: Raymond V. Damadian, Woodbury, NY (US); Luciano B. Bonanni, Dix Hills, NY (US)

(73) Assignee: Fonar Corporation, Melville, NY (US)

( * ) Notice: Subject to any disclaimer, the term of this patent is extended or adjusted under 35 U.S.C. 154(b) by 594 days.

(21) Appl. No.: 16/426,128

(22) Filed: May 30, 2019

Related U.S. Application Data (63) Continuation of application No. 16/381,778, filed on Apr. 11, 2019, now abandoned.

(60) Provisional application No. 62/656,467, filed on Apr. 12, 2018.

(51) Int. Cl.
| | |
|---|---|
| *A61B 5/00* | (2006.01) |
| *A61B 5/055* | (2006.01) |
| *A61B 17/34* | (2006.01) |
| *A61B 18/20* | (2006.01) |
| *G01R 33/38* | (2006.01) |
| *A61B 18/00* | (2006.01) |

(52) U.S. Cl.
CPC ............ *A61B 5/055* (2013.01); *A61B 5/0036* (2018.08); *A61B 5/4566* (2013.01); *A61B 5/702* (2013.01); *A61B 17/3403* (2013.01); *A61B 18/20* (2013.01); *G01R 33/3806* (2013.01); *A61B 2018/00339* (2013.01)

(58) Field of Classification Search
CPC ..... A61B 5/055; A61B 5/0036; A61B 5/4566; A61B 5/702; A61B 17/3403; A61B 18/20; A61B 2018/00339
See application file for complete search history.

(56) References Cited

U.S. PATENT DOCUMENTS

| | | | |
|---|---|---|---|
| 7,123,008 B1 * | 10/2006 | Damadian ......... | G01R 33/3806 324/309 |
| 9,386,939 B1 * | 7/2016 | Minkoff ........... | G01R 33/56383 |
| 9,766,310 B1 * | 9/2017 | Damadian ........ | G01R 33/34046 |

* cited by examiner

*Primary Examiner* — Joel Lamprecht
(74) *Attorney, Agent, or Firm* — Lerner, David, Littenberg, Krumholz & Mentlik, LLP (57) ABSTRACT

A system including a magnetic resonance imaging system having a magnet and first and second sidewalls positioned on opposite sides of an imaging field of the magnet, and a subject support configured to support a subject that is positioned in an upright position. The system may be capable of imaging a target anatomy of the subject while the subject is in the upright position, and may further include a motor for translating the subject support between first and second positions within and outside of the imaging field of the magnet, respectively. The subject support may include a seat on which the subject may sit facing the subject support, such that the subject's back can be operated on and imaged while the subject is in an upright position.

22 Claims, 6 Drawing Sheets

VISUALIZATION OF SPINAL ABNORMALITY USING UPRIGHT MR IMAGING DURING SPINAL TREATMENT

CROSS-REFERENCE TO RELATED APPLICATIONS

The present application is a continuation of U.S. patent application Ser. No. 16/381,778, filed Apr. 11, 2019, which claims the benefit of the filing date of U.S. Provisional Patent Application No. 62/656,467 filed Apr. 12, 2018, the disclosures of which are hereby incorporated herein by reference.

TECHNICAL FIELD

This disclosure relates to methods and systems for visualizing a subject's anatomy during an operation such as spinal surgery using an upright magnetic resonance imaging (MRI) apparatus.

BACKGROUND

Magnetic Resonance Imaging has proven to be a valuable technique in providing visualization and guidance during surgical procedures. Presently, a surgical procedure performed in conjunction with MR imaging might be conducted as follows: An MRI study of an anatomical region of interest would be performed in a conventional recumbent-magnet MR imaging system in order to provide baseline information prior to initiation of a surgical procedure. After the initial imaging evaluation, the subject would be removed from the magnet and the surgical intervention would take place. The subject would then be replaced into the scanner magnet in order to assess the status of the surgical procedure and whether any additional surgery is desirable or required at that time. This sequence of imaging followed by surgery and followed again by imaging would be repeated as many times as necessary until a surgeon was satisfied that the goal for a particular surgical procedure had been achieved.

Surgery performed in this fashion presents a number of difficulties which impact the surgical process and are impediments to a successful surgical outcome. For example, a subject is typically placed inside the bore of a recumbent solenoidal magnet for the MR imaging portions of the surgical procedure. The magnet bore is a very confined space which does not allow access to a subject by the surgical team, and is what makes it necessary to remove the subject from the magnet in order to perform the surgery. Second, as a consequence of this, the subject cannot be imaged during the surgical portion of the procedure in order to achieve a real time visualization of the procedure's effectiveness. That is, the MR Imaging and surgical intervention portions must occur sequentially. Thirdly, such a procedure involving repeated removal and insertion of a subject into and out of the MRI magnet can be very time consuming, which lengthens the overall time of the procedure and increase risks to the subject undergoing surgery. In addition, for more intricate surgical procedures moving the subject from the operating theatre is not a possibility.

Advanced technology exists for the treatment of spinal abnormalities via use of a laser. Laser treatment has proven highly effective, for example, in performing diskectomies in the spine or removing spinal disk herniations that are compressing or compromising spinal nerve roots. Laser treatment has conventionally been performed while the subject is in a recumbent and non-weight bearing position. However, performing the treatment in such a position is disadvantageous, since one cannot visualize the disc herniation in the fully weight-bearing body position of the subject during the treatment. This makes it more difficult to visualize the maximum degree of disc herniation that the subject experiences (e.g., when the subject is upright instead of recumbent), which in turn makes it more difficult to optimize treatment and directly address the subject's spinal disc herniation in the subject's most pronounced spinal disc herniating body position. The same difficulties can be true for other minimally invasive treatments performed on a subject in a recumbent position.

SUMMARY

In contrast to conventional MR systems that contain a solenoidal magnet design for imaging the recumbent subject as described above, an upright MR scanner facilitates positioning a subject in multiple weight-bearing as well as non weight-bearing orientations. Furthermore, the subject can be oriented and reoriented among these positions without having to unharness and re-harness the subject in the support apparatus of the imaging and treatment apparatus. Furthermore, the upright MR scanner facilitates access to the subject for the purpose of performing an operation, so the operation and imaging can be done while the subject is harnessed in the same apparatus. This can improve both the accuracy and the efficiency of operating and imaging procedures.

In one aspect, the present disclosure is directed to a system including a magnetic resonance imaging system and an open space. The imaging system may include a magnet; first and second sidewalls positioned on opposite sides of an imaging field of the magnet, and a subject support configured to support a subject that is positioned in an upright position. The magnetic resonance imaging system may be capable of imaging a target anatomy of the subject while the subject is in the upright position. The open space may be configured to permit access to a person operating on the subject's back while the subject is in the upright position. A first motor may be included for translating the subject support between first and second positions, the first position being within the imaging field of the magnet (such that the target anatomy of the subject is capable of being imaged while the subject is in the upright position) and the second position being outside of the imaging field and in the open space. Additionally, the subject support may be between the first and second sidewalls in the first position (such the subject is accessible to a person only from the subject's posterior direction), and the subject support may be displaced from between the first and second sidewalls in the second position (such the subject is accessible to persons on the subject's sides).

In some examples, the system may include a second motor configured to rotate the subject support between a first rotational position and a second rotational position, the magnetic resonance imaging system being configured to image the subject in the first rotational position and the subject being capable of being operated on when the subject is in the second rotational position. The first rotational position may be an upright position and wherein the second rotational position may be a recumbent position. The first motor and the second motor may be the same motor or different motors.

In some examples, the first position and the second position may be between one to four feet apart. The first position may be within an imaging region of a magnet of the magnetic resonance imaging system, and the second position may be within view of an operating theatre gallery. In some examples, the open space may be within a frame of the magnet such that multiple people can operate on the subject's back from the open space.

In some examples, the subject support may include a seat assembly adapted to support the subject in an upright sitting position. The seat assembly may affixed to a bed of the subject support, and may be adapted to support the subject in the upright sitting position with the subject facing the bed of the subject support (such that a surgeon has access to the subject's back). The seat assembly further may further include a fixture for supporting a portion of the subject's upper body.

Another aspect of the disclosure is directed to an apparatus for positioning a subject in an upright sitting position. The apparatus may be configured to be mounted to a bed that is mounted to a support surface, a bottom surface of the bed facing the support surface when the bed is in a partially upright or flat position, and a top surface of the bed facing away from the support surface when the bed is in a partially upright or flat position. The apparatus may include a first extension member extending upward from a first location in a direction away from the platform and away from the bed, the first location being located a first distance from the bed, a second extension member extending upward from a second location in a direction away from the platform and towards the bed, the second location being located a second distance from the bed that is greater than the first distance, a first subject receiving surface mounted to the first extension member, a top surface of the first subject receiving surface facing away from the first extension member and adapted for a subject to sit on, and a second subject receiving surface mounted to the second extension member, a top surface of the second subject receiving surface facing away from the second extension member and being adapted for the knees of the subject to rest on.

The top surface the first subject receiving surface may be angled towards the bed, and the top surface of the second subject receiving surface may be angled away from the bed. The second subject receiving surface may contact the top surface of the bed.

In some examples, at least one of the first distance or the second distance may be adjustable.

In some examples, the first extension member and the second extension member may intersect at an intersection point, and the intersection point may be adjustable.

In some examples, the second subject receiving surface may include a gap, and the first extension member may extend from a mounting bar to the first subject receiving surface through the gap.

In some examples, the second extension member may include a plurality of grooves, and the apparatus may include a stand extending from the first extension member. The stand may include a first end hingedly coupled to the first extension member, and a second free end adapted to engage one or more of the plurality of grooves of the second extension member to lock the first and second support surfaces in place relative to one another.

In some examples, the apparatus may include a vertical shaft extending upward from the second subject receiving surface, and a horizontal shaft coupled to the vertical shaft. The horizontal shaft may be adapted to support the subject's arms when the subject is seated on the apparatus.

In some examples, the apparatus may include a platform mounted to the bed at a fixed point and having a length extending substantially perpendicularly from the top surface of the bed, the platform having an upper surface facing most of the bed, a first support bar positioned on the upper surface of the platform across a width of the platform at the first location, the first extension member extending therefrom and supported by the first support bar, and a second support bar positioned on the upper surface of the platform across the width of the platform at the second location, the second extension member extending therefrom and supported by the second support bar. The width of the platform may be substantially equal to a width of the bed, and each of the first and second support bars may have a length substantially equal to the width of the platform.

In some examples, the apparatus may further include the bed.

Another aspect of the disclosure is directed to a system including any of the above-described apparatuses, and a magnetic resonance imaging system configured to image a subject sitting on the apparatus in an upright position.

Yet another aspect of the disclosure is directed to a system including a magnetic resonance imaging system and a treatment apparatus. The MRI system may include a subject support configured to support a subject positioned in an upright position. The magnetic resonance imaging system may include a magnet capable of imaging a target region of the subject within a field of view of the magnet. The subject support may be positioned within the field of view of the magnet. The treatment apparatus may include a handheld treatment component adapted to be pointed at the target region of the subject in the field of view of the magnet while the subject is supported by the subject support in the upright position. The treatment component may be one of a laser or a needle.

DETAILED DESCRIPTION

The UPRIGHT® MR scanner has a magnet with a horizontally-oriented magnetic field and is used in conjunction with a subject positioning system which can translate in two dimensions, as well as rotate. Thus, when a subject is located on the subject positioning system, they may be positioned upright, recumbent, or at any angle in between. In addition, when upright, the subject may be standing or seated so as to be weight-bearing.

Typically, when a subject is in a vertical or weight-bearing position in the UPRIGHT® MR scanner, for the purposes of MR imaging, he/she is facing frontally with their back placed against the surface of the positioning system bed. In the present invention, the subject is rotated 180 degrees so he/she is facing the bed and the full length of the spine and back is now facing outward toward the treating physician. Preferably, the subject would be standing or seated in this reverse orientation position and furthermore, could simultaneously be inside the magnet for the purposes of imaging. Importantly, in this reverse orientation, the surgeon would have full access to the back and spine for performing surgical procedures in the same body position that the images are being obtained.

Figure 1:
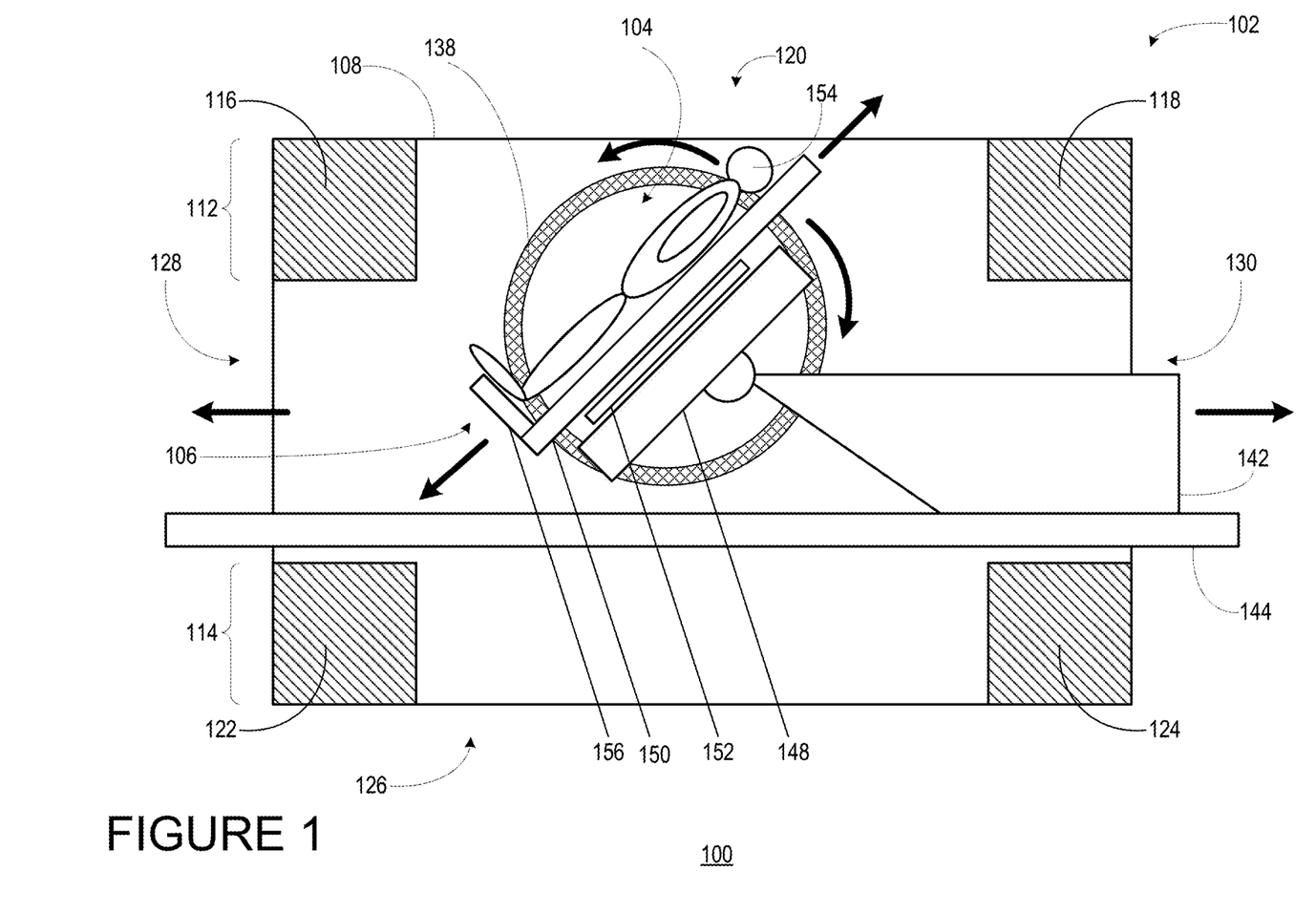
FIG. 1 depicts an MRI apparatus in accordance with an aspect of the disclosure.

An example upright MR imaging apparatus 100 is shown in FIG. 1. In one embodiment, the MRI apparatus 100 includes a magnet having a ferromagnetic frame 102, a magnetic flux generator 104, and a subject handling system 106. The ferromagnetic frame 102 includes a first side wall 108 and a second side wall. The side walls extend vertically. As FIG. 1 is a sectional view of the MRI apparatus 100, FIG. 1 does not show the second side wall or any of its associated structures for clarity. The second side wall would include all the components necessary to complete the path for a magnetic circuit or loop, e.g., a corresponding pole or an electromagnetic coil assembly to that shown in FIG. 1 with reference numeral 138, etc.

The ferromagnetic frame 102 may also include a top flux return structure 112 and a bottom flux return structure 114. The top flux return structure 112 may include two columnar structures 116 and 118. Between these two columnar structures, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 defines a front subject opening 128 on one side of the frame and a similar back subject opening 130 on the opposite side of the frame.

The ferromagnetic frame further includes a first magnetic pole and a second magnetic pole. The first magnetic pole extends from the first side wall 108 towards the second side wall and the second magnetic pole extends from the second side wall towards the first side wall 108. The magnetic poles are generally cylindrical and are coaxial with one another on a common horizontal polar axis. Between the magnetic poles is a gap accessed by the front subject opening 128, the back subject opening 130, the top opening 120 or the bottom opening 126.

The magnetic flux generator 104 includes a first electromagnetic coil assembly 138 magnetically coupled to ferromagnetic frame 102, proximate to side 108, and parallel to side 108. The magnetic flux generator 104 also includes a second electromagnet coil assembly (not shown) magnetically coupled to ferromagnetic frame 102, proximate to the second side wall, and parallel to the second side wall. As previously noted, these electromagnetic coil assemblies 138 may be either resistive or superconductive. Alternatively, the magnetic flux generator 104 may be a permanent magnet. The magnetic flux generator 104 may be configured to emit a magnetic field Bo along one or more axes. The magnetic flux generator 104 may also include one or more gradient coils (not shown) for inducing a gradient in the Bo magnetic field. The Bo magnetic field generally extends horizontally parallel to support surface of the apparatus from one side wall to the other. The support surface will generally be the floor of a building or facility housing the apparatus 100.

The apparatus 100 may further include a subject support assembly 106 including a chair or seat assembly on which a subject is capable of sitting. The subject handling system 106 is capable of three degrees of motion. The subject handling system further supports positioning of a subject in the Trendelburg and reverse-Trendleburg orientations. Generally, the degrees of motion allow for positioning of the subject in a variety of orientations or positions. The subject handling system 106 may include a carriage 142 mounted on rails 144. The carriage 142 may move linearly back and forth along the rails 144. The rails 144 typically do not block the bottom open space 126.

A generally horizontal pivot axis is mounted on carriage 142. An elevator frame 148 is mounted to the pivot axis. The carriage 142 is operable to rotate the elevator frame 148 about the pivot axis. A subject support 150 is mounted on the elevator frame 148. The subject support 150 may be moved linearly along the elevator frame 148 by an actuator 152. Thus, a subject 154 can be positioned with a total of three degrees of freedom, or along three axes of movement. Specifically, the subject handling system 106 can move a subject 154 in two linear directions and also rotate subject 154 around an axis. The solid black arrows of FIG. 1 show various axes of movement possible with the subject handling system 106. Note that often the rails 108 are mounted such that portions of subject 154 may be positioned below the rails through bottom open space 126.

The apparatus 100 may be configured such that the seat assembly is not present. In that configuration, the subject 154 would then be allowed to stand on the support 156. Allowing the subject to sit or stand, or more generally to remain in an upright position during imaging, may have advantages. For example, blood and CSF flow may be different in the upright position than in a recumbent position and may reveal abnormal conditions that would not be revealed while the subject is in the recumbent position.

In making MRI measurements, the subject may be fitted with an antenna coil that receives magnetic resonance signals from the region of interest of the subject's anatomy being imaged. Such antennas may be placed at on or proximate the subject and may include a variety of geometries that maximize the signal strength and signal-to-noise (S/N) ratios of the magnetic resonance signals emitted by the anatomy of interest. Such antennas may include head coils to capture image signals associated with the head, neck or upper spine. Other antennas may include coils that are place proximate the back or spinal column.

Additional views and descriptions of an upright MRI apparatus may be found by reference to U.S. Pat. No. 6,677,753, the disclosure of which is incorporated herein by reference. Alternative embodiments of the upright MRI apparatus also include those discussed in U.S. Pat. No. 6,414,490, the disclosure of which is also incorporated by reference. In addition, the upright MRI apparatus does not necessarily need to include ferromagnetic frames or poles. For example, an apparatus such as that disclosed in commonly assigned U.S. Pat. No. 8,384,387, the disclosure of which is incorporated by reference herein, may comprise the MRI apparatus in accordance with the various aspects of the present disclosure.

Figure 2:
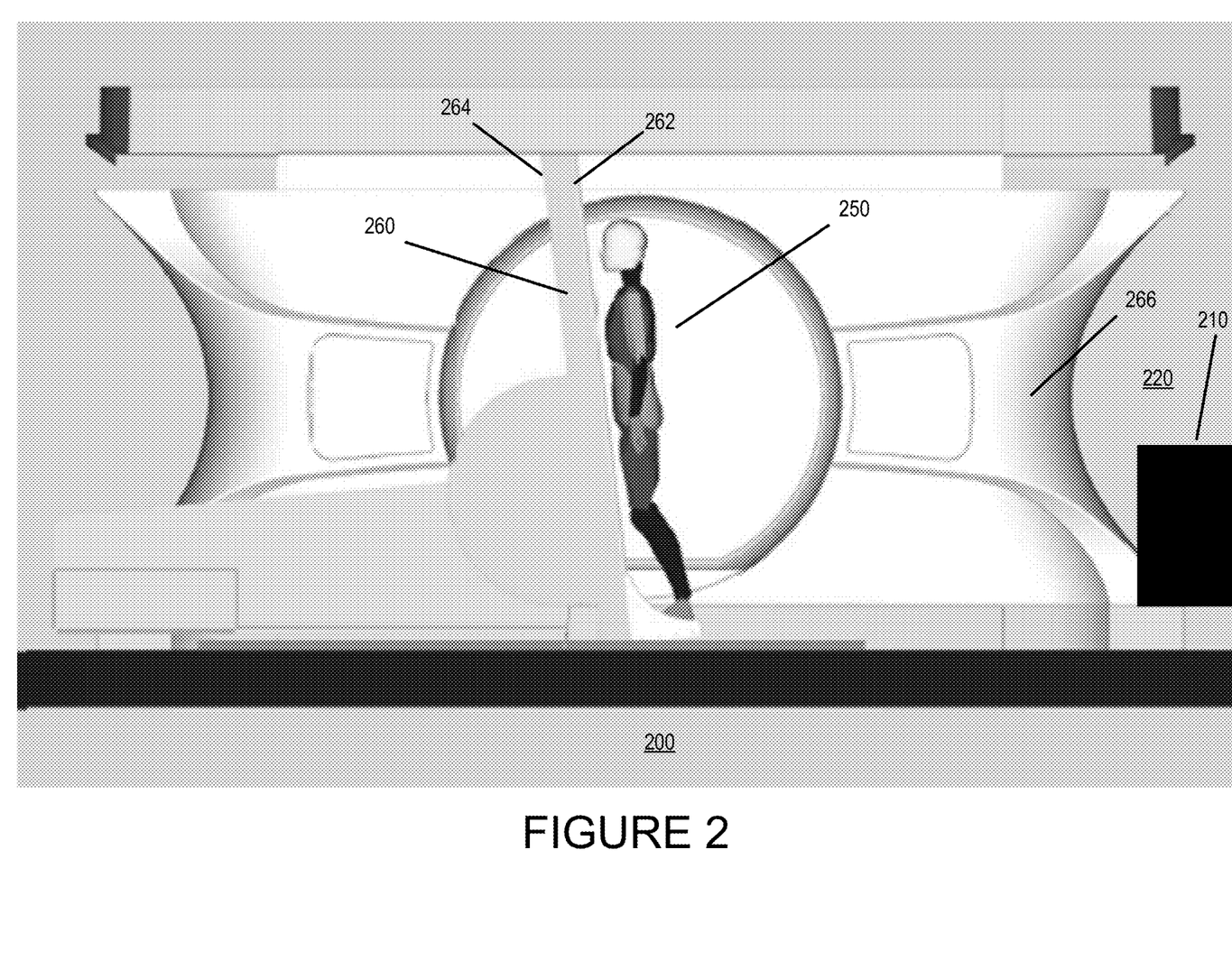
FIG. 2 depicts a system in accordance with an aspect of the disclosure.

The upright MRI apparatus 100 may be incorporated into an MRI system 200. The MRI system 200 may include additional components to facilitate operation on a subject. For instance, the MRI system 200 may be conducive for the treatment of spinal abnormalities using a laser. In this regard, the MRI system 200 may include a laser treatment apparatus 210. The laser treatment apparatus 210 may include a power source connected to a handheld laser, such as by a flexible cable. A surgeon or other person may hold the laser in order to operate on a subject positioned in the MRI system 200. The subject may be positioned such that the laser can be directed towards the subject while the subject is positioned in the imaging field (also referred to as the field of view or FOV) of the upright MRI apparatus 100. Inclusion of both the laser treatment apparatus 210 and upright MRI apparatus 100 in the system 200 may facilitate treating a target anatomy of the subject and imaging the subject's target anatomy, without having to move the subject between positions.

In the case of a subject that is treated within the imaging field of the apparatus 110, it may be possible for only a single person to access and thus directly treat the subject. This is because the area allowing access to the subject is restricted due to the design of the magnet structure, and in particular the presence of sidewalls on either side of the subject. The space between the sidewalls may be about 18 inches, sufficient for the subject to occupy but not for another person to stand on the side of the subject. Therefore, access to the subject may be only from behind the subject as the subject is facing the support. Nonetheless, even if only one person can directly access the subject for treatment, it may be possible for other people (e.g., assistants, clinicians) to stand close by to the one person with direct access, and even within an open space 220 within the frame of the apparatus 100. In the above manner, the subject could be imaged and operated on without having to be moved at all.

Alternatively, in some instances, it may be preferable to operate on the subject in one position and to image the subject in a different position. For instance, it may be preferable to image the subject while upright, but to operate on the subject while recumbent. In such a case, inclusion of both the laser treatment apparatus 210 and the upright MRI apparatus 100 in the system 200 may facilitate a controlled movement of the subject between those two positions, such that the subject's position can be alternated (e.g., from surgery to imaging and back to surgery, from imaging to surgery and back to imaging) without altering the subject's respective positions in each of those positions. That is to say, if the subject were imaged at a first time, moved out of the imaging position and then back into the imaging position, and then imaged at a second time, the system 200 would ensure that the position of target anatomy at each of the first time and the second time is the same. In some instances, ensuring that the position of a target anatomy has not changed can be essential for evaluating the subject's condition and how it has changed. In this regard, the above-described system 200 may allow for changes in the subject's condition can be monitored throughout surgery.

As noted above, the MRI system 200 may also include an open space 220 large enough to accommodate one or more surgeons or other people. The surgeons and people may be able to operate on or otherwise access the subject during an operation, as necessary. In other instances, the laser treatment apparatus 210 may be relied on to perform the operation, making other forms of access to the subject unnecessary. In such instances, the open space 220 may be omitted, so long as there is sufficient space for the subject to access the system and for a laser ray emitted from the laser of the treatment apparatus 210 to pass into the MRI apparatus 200 to a target anatomy of the subject.

In the example of FIG. 2, a subject 250 is shown standing in a reverse orientation position in the upright MRI apparatus 100, meaning that the subject 250 is facing the subject support 260. The subject support 260 may keep the subject in the standing position, as shown in FIG. 2, during both a surgical procedure and imaging. The subject support 260 may be a bed or slab on which the subject is harnessed. The support 260 may have a top surface 262 on which the subject 250 is positioned and a bottom surface 264 opposite the top surface 262.

Additionally, the subject support 260 may be connected to one or more motors (not shown) capable of moving the support 260. For example, the bottom surface 264 of the support 260 may be mounted to, supported by, or otherwise rest on a wheel, rail or both, and the one or more motors may control a movement along the wheel, rail or both. The wheel (e.g., one or more gears, hinges, axels, etc.) may be used to pivot an orientation of the support 260, which by extension may cause rotation of a subject 250 harnessed or otherwise fastened to the support 260. The rail may be used to guide a translation of the support 260, which by extension may cause a controlled displacement of the subject 250 in the support 260.

The support 260 may be translated vertically or horizontally in order to move the subject 250 into and out of an imaging region of a magnet concentrated between the two poles of the upright MRI apparatus 100. The subject support 260 may be advanced towards the front area 266 of the system that is the area adjacent to the posterior of the subject 250 (e.g., in the example of FIG. 1, through the front opening 128). This movement of the subject may bring the subject 250 to the front area 266 location of the system 200, whereby even more than one surgeon may be able to access the anatomy of interest for an operation even while a portion of the subject's anatomy (e.g., head and upper back or torso area) is still located within the frame system 200. This is because moving the subject 250 towards the front area 266 may also move the subject 250 out from between the sidewalls on either side, thus providing direct access to the subject 250 from the side instead of only from directly behind the subject 250. In addition, the open area 220 may be sufficiently large for the surgeons and other people to be capable of performing a required operation or surgical procedure from the open area 220 while the subject is located in the front area 266, with multiple people being capable of directly accessing the subject 250.

In some examples, translating the support 260 may involve moving the support 260 between one to four feet. This distance may correspond to a length of a canopy of the apparatus positioned above the subject, whereby moving the subject out from underneath the canopy of the apparatus may make the subject visible to people present above the apparatus and operating area, such as people in an operating theatre. In this regard, moving the subject may involve the support 260 being moved between an imaging field (e.g., with the FOV) and an operating theatre, and the open area 220 may be sufficiently open to provide a view of the subject from the operating theatre seating when the subject is in the open area 220. Thus, it may be possible to perform an operation that is viewable to students or other spectators and to image the subject without requiring the subject to move on their own.

Additionally or alternatively, the support 260 may be pivoted, reoriented, or otherwise rotated. Rotating the subject may involve moving the subject between upright and not upright positions. The upright position may be a position that is both weight bearing and comfortable for the subject. For example, in FIG. 2, the subject is shown in an almost but not entirely vertical position (e.g., about a 10-30 degree incline). However, the subject may be rotated to a less vertical position during the operation but for imaging may be rotated to the position shown for imaging since the weight bearing position may reveal characteristics of the spine or muscles within the lower back in a weight bearing position as a opposed to a recumbent position. For example, in the weight bearing position discs may compress more, and imaging may reveal such details in effect in real time, which would then serve as active feedback that a surgeon may use in performing an operation or correcting a procedure during an ongoing operation.

Alternatively, a subject may be seated on a subject support in a reverse orientation position in a magnetic imaging apparatus. In such an example, the subject support may equipped with a seat that allows for the subject to be seated, such that the operation or surgical procedure may be performed and imaging may take place with the subject remaining in the seated position. The seat may be fastened or otherwise mounted to the subject support, and thus may be rotated or translated with the subject support in the manner described above. For a subject that is unable to stand, or for a subject that cannot stand for the time required to perform the operation or surgical procedure, seating the subject may provide an alternative that includes all or most of the advantages over positioning the subject in a recumbent position, as discussed above.

Figure 3:
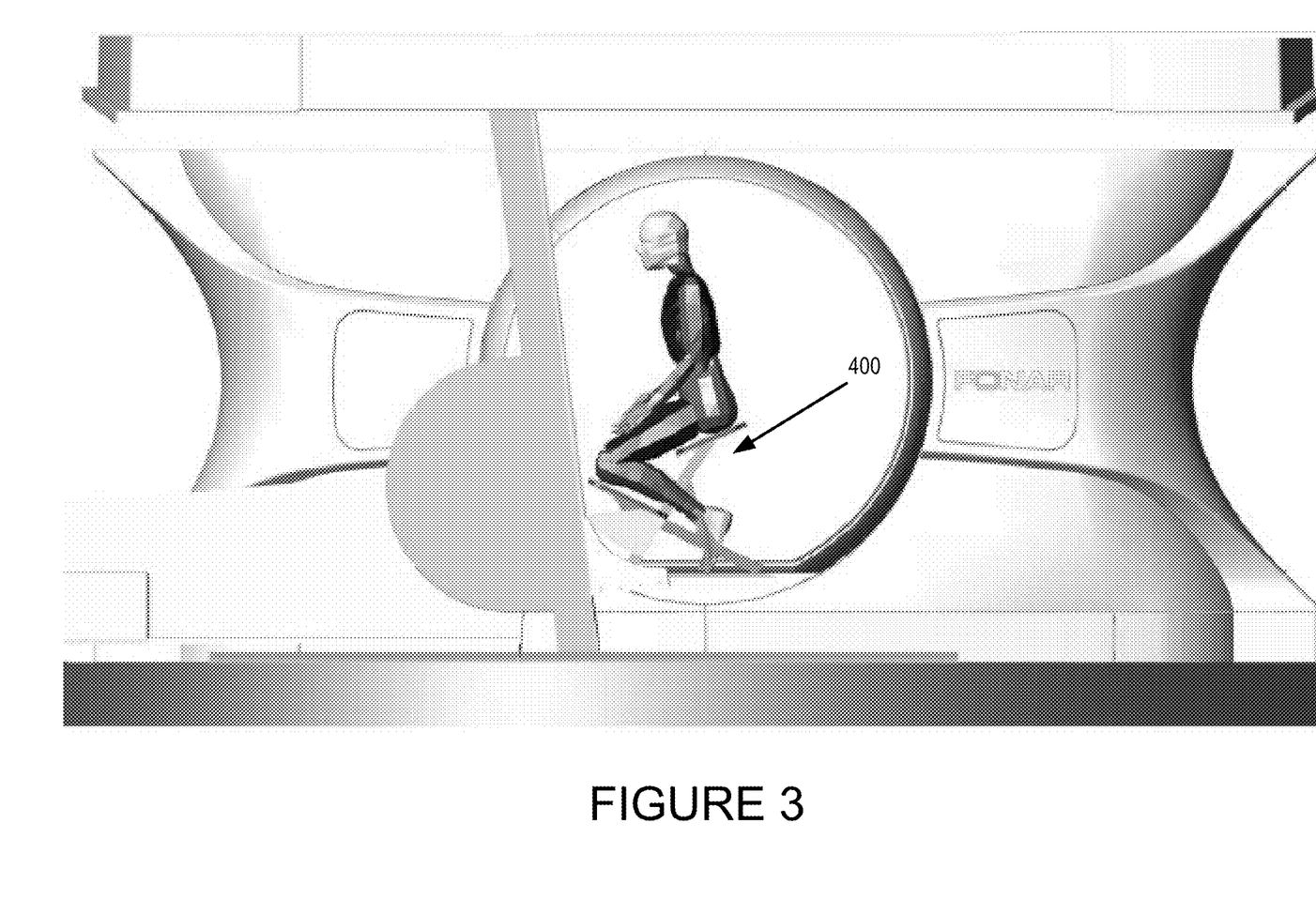
FIG. 3 depicts another system in accordance with an aspect of the disclosure.
Figure 4:
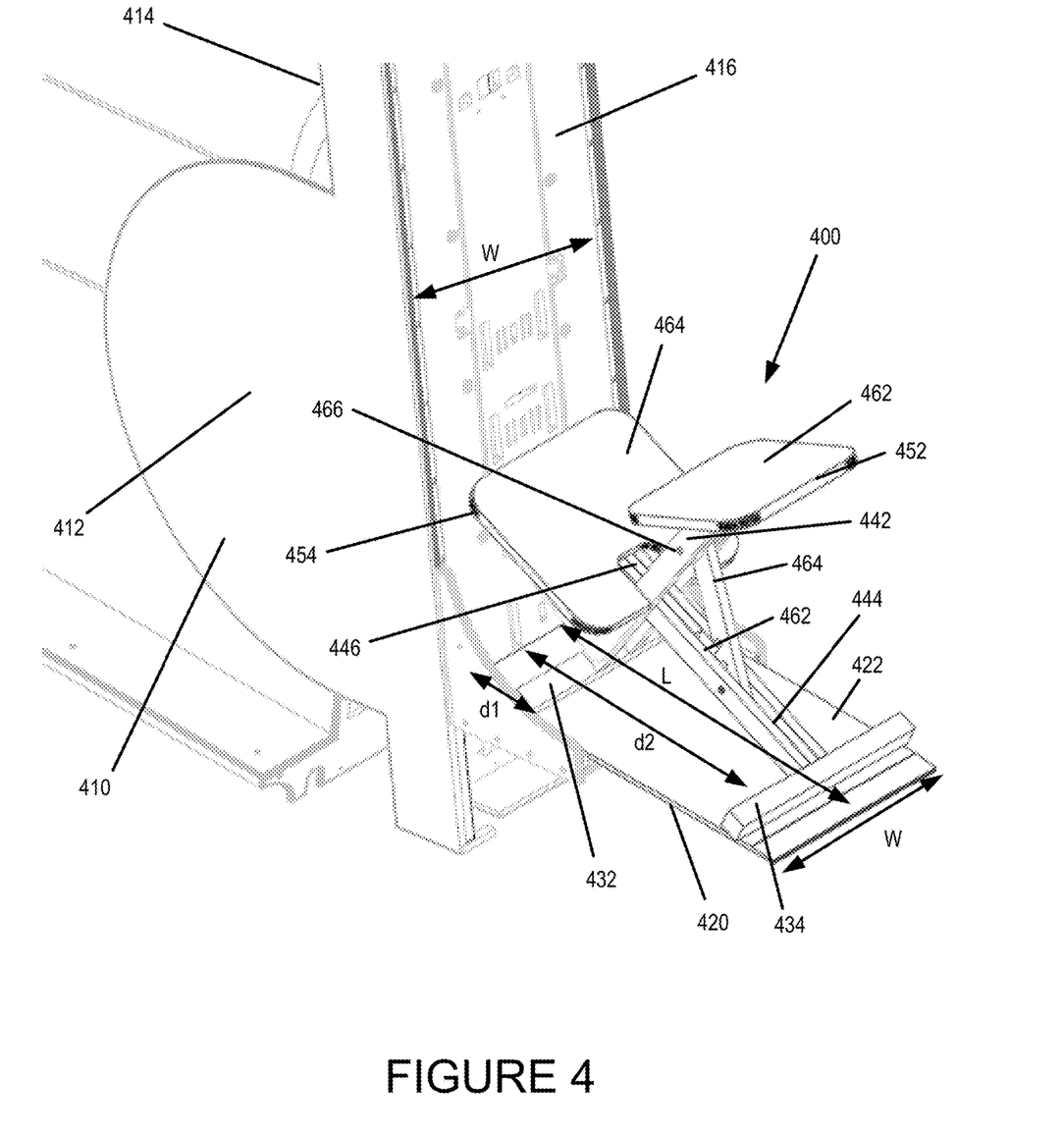
FIG. 4 depicts an example positioning apparatus for use in the system of FIG. 3.

FIGS. 3 and 4 illustrate a first example seat 400 for supporting an upright subject. FIG. 3 shows a side view of a system including a seat occupied by a subject in an upright seated position. FIG. 4 shows a perspective view of a vacant seat of the system of FIG. 3.

As shown in FIG. 4, the seat 400 may be configured to be mounted to a support 410, such as a bed on which a subject normally lies down. The support 410 may itself be mounted to a support surface (not shown). The support 410 may further be configured to pivot about a pivot point 412, as described above in connection with FIG. 2. For example, the support 410 may rotationally move between an upright position (in which a subject resting on the support is supported in an upright or nearly upright position) and a recumbent or flat. For further example, the support 410 may pivot between fully and partially upright positions, or between two partially upright positions (one having a slope steeper than that of the other). A bottom surface 414 of the support 410 faces the support surface in the partially upright and flat positions, and a top surface 416 of the support 410 faces the opposite direction.

The subject may be supported by the support 410 even when it is on an incline, including a steep incline for which the subject is nearly upright. Thus, the support 410 may include a platform 420 on which the seat 400 may rest. In the example of FIG. 4, the platform 420 is shown as extending in a direction substantially perpendicular to the surfaces 414, 416 of the support 410, although in other examples, the planes of the platform 420 and the support surfaces may form an angle other than 90 degrees. In the example of FIG. 4, the substantial perpendicularity is sufficient to provide a base on which the seat 400 may rest and properly support the subject even when the support 410 is vertical or nearly vertical (e.g., the subject is in an upright or nearly upright position). The platform 420 may be mounted to the support 410 at a fixed point, and may extend across a full width W of the platform 410.

An upper surface 422 of the platform 420 may support two or more support bars 432, 434. Each support bar 432, 434 may also extend across a full width W of the platform 420 at varying distances from the support 410. For instance, the first support bar 432 may be positioned at a first distance d1 from the support 410, and the second support bar 434 may be positioned at a second distance d2, different from d1 (e.g., greater than d1), from the support 410.

In the example of FIG. 4, the support bars 432, 434 rest on top of the platform 420, but are not otherwise affixed to the platform 420. This may allow adjustment of the support bars 432, 434 so that the seat 400 can be adjusted from subject to subject. In other examples, the support bars 432, 434 may be affixed to the platform in a given position.

Each of the support bars 432, 434 may support a respective extension member 442, 444. The extension members 442, 444 may extend away from the support bars 432, 434 and away from the platform 420 towards a receiving surface of the seat 400. In essence, the support bars 432, 434 may function as feet of the seat by providing balance on the platform 420, while the extension members 442, 444 may function as legs of the seat 400, providing a given height, and the receiving surface is a cushion of the seat 400, providing comfort for a person sitting on the seat 400. In this manner, adjusting one or more of the support bars 432, 434 may cause a height adjustment of the support surface of the seat 400.

The first extension member 442 may extend from the first support bar 432. The direction of the extension may be on a diagonal relative to each of the platform 420 and the support 410, such as away from the platform 420 and away from the support 410. Similarly, the second extension member 444 may extend from the second support bar 434 diagonally relative to the platform 420 and support 410, such as away from the platform 420 and towards the support 410. The result of may be the two extension members 442, 444 crossing one another diagonally at an intersection point. Height adjustments may be performed by bringing the support bars 422, 424 closer to one another or farther apart, as in a scissor lift (e.g., making support bars closer raises the seat, spacing the support bars farther apart lowers the seat). In this manner, the intersection point between the two extension members 442, 444 may also be adjusted, whereby a lower intersection point may result in a lower seat height, and a higher intersection point may result in a higher seat height.

The receiving surface for supporting a weight of the patient may be divided into sections. In the example of FIG. 4, a first surface 452 is mounted to the first extension member 442. The first surface 454 may be adapted for a subject to sit on (e.g., on the part of the surface facing away from the first extension member 442 and platform 420). Similarly, a second surface 454 is mounted to the second extension member 444, and the second surface 454 may be adapted for the subject's knees to be positioned thereon (e.g., on the part of the surface facing away from the second extension member 444 and platform 420).

The respective surfaces 452, 454 may be angled or otherwise contoured in order to provide a comfortable seating surface for the subject. For instance, as shown in FIG. 4, the first surface 452 may be angled such that a top surface 462 faces towards the support 410. In this manner, sitting on the first surface 452 may cause the subject to lean forward towards the support 410. For further instance, as also as shown in FIG. 4, the second surface 454 may be angled such that its top surface 464 faces away from the support 410. In this manner, placing one's knees on the second surface 452 may involve the second surface 454 pushing back against the subject's knees so that the subject does not slide forward and off of the first support 452. The combined support from the first and second surfaces 452, 454 may help to keep the subject in a steady and comfortable position, while also maintaining the subject in a slightly forward leaning position. The forward leaning position may be beneficial for conducting the subject's operation or surgery. For instance, in the case of a back operation, the forward leaning position may improve access to various parts of the subject's back anatomy.

In order to improve stability of the seat (and thus stability of the subject sitting on the seat), further design considerations may be taken into account in the design of the seat 400. For example, at least a portion of the seat 400 may be supported by support 410. Thus, the support 410 and platform 420 may both provide support to the seat 400. In one such example, the second surface 452 may be in contact with a portion of the support 410. Thus, when a subject rests their knees on the second surface 452, the support 410 may prevent the force of the subject's knees from pushing the second surface 452 forward. In some examples, the second surface 452 may even be mounted or locked into place with the support 410 to prevent such sliding.

Additionally, in the example of FIG. 4, both the first and second support bars 432, 434 are shown as resting freely on the platform 420. However, in other examples, one of the support bars 432 may be affixed in place to the support 410 while the other support bar free slides back and forth along the length L of the platform 420. In this manner, the affixed support bar may provide additional stability, while the height of the seat may still be freely adjusted by varying the distances between the first and second support bars 432, 434 as in a scissor lift.

In order to further improve stability, the two extension members 442, 444 may be interlocked with one another. In one example, a hinge may be provided such that a relative angle of the two extension members may vary at the hinge. The hinge may further include a groove in one extension member along which a protrusion of the other extension member extending into the groove may slide. In this manner, the intersection point of the extension members may still be adjustable. In the particular example of FIG. 4, one of the extension members (e.g., the second extension member 444) may include an aperture 446 or gap through which the other extension member (e.g., the first extension member 442) passes, thus extending from the first support bar 432 to the first surface 452 through the gap 446. This may prevent the two extension members 442, 444 from laterally separating apart from one another, while still permitting for an adjustment to the angle formed between the two members.

To provide further stability as well as adjustability, the extension members may be adapted to include one or more protrusions that may selectively fit into one or more discrete grooves or notches in order to fix the extension members into place. The extension members may be adjusted in the manner described above in order for different protrusions to fit into the respective grooves or notches. In the example of FIG. 4, the second extension member 444 is shown including a plurality of rungs 462, and the first extension member 442 is shown including a hinged protrusion 464 or stand having a first end hingedly coupled to the first extension member 442 by a hinge 466 and a second free end including a plurality of grooves for engaging the rungs 462. When the protrusion 464 is inserted into one of the rungs 462, the second extension member 444 becomes locked in place, and thus the support surfaces 452, 454 are also locked in place and do not slide apart. In other examples, the rungs and grooves may be switched such that the grooves are positioned on the second extension member 444.

In other examples, stability may be provided by mounting the seat directly to the support 410. In this case, the support, may include a bar onto which the seat may be hooked. The hooks may be included at a lower end of the first extension member, and may be downward facing, such that the weight of the subject sitting on the first surface may provide a force for the hooks to engage the bar on the support. For example, the seat in FIG. 6, described in greater detail below, includes downward facing hooks 680 that may engage a bar on a subject support. In this case, the extension members may still be hingedly coupled to each other and may still be adjustable in the manner described above, but the platform and support bars may no longer be necessary to support the weight of the subject.

In order to provide further stability for a subject positioned on the seat, fixturing may be provided. The fixturing may provide support for the subject's upper body or torso, thus preventing the subject from twisting, slouching, or otherwise moving their upper body and torso during the operation. The stability and comfort provided to the subject's upper body by the fixturing may be in addition to the stability and comfort provided to the subject's lower body by the seat.

Figure 5:
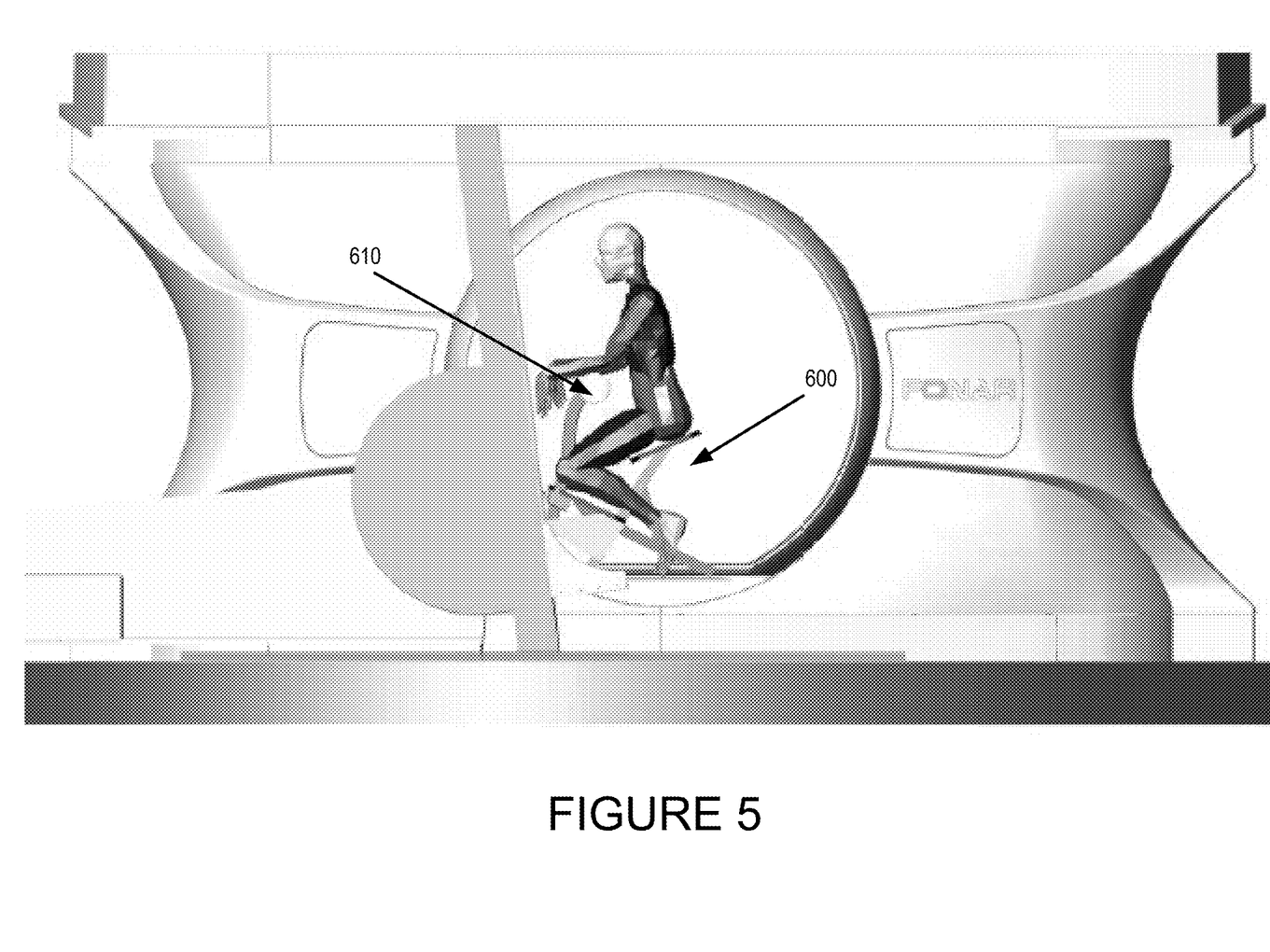
FIG. 5 depicts another system in accordance with an aspect of the disclosure.
Figure 6:
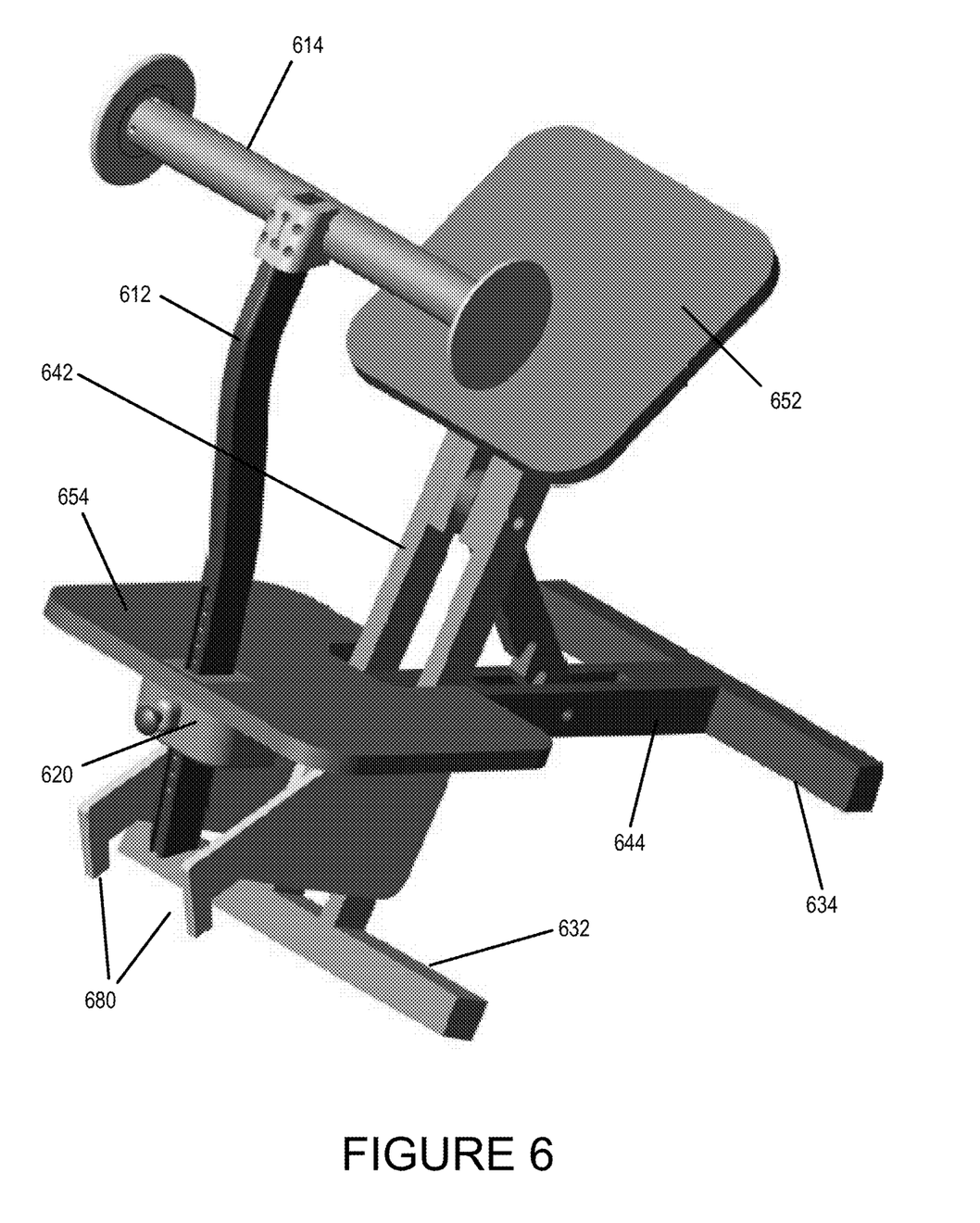
FIG. 6 depicts an example positioning apparatus for use in the system of FIG. 5.

FIGS. 5 and 6 illustrate a second example seat 600 for supporting an upright subject and including fixturing. FIG. 5 shows a side view of a system including seat occupied by a subject in an upright seated position. FIG. 6 shows a perspective view of a vacant seat of the system of FIG. 5.

The example seat 600 is comparable to that of FIG. 3, and may include many of the same or similar features, such as support bars, 632, 634, extension members 642, 644, and surfaces 652, 654. In the example of FIG. 6, the fixturing 610 includes a vertical shaft 612 extending from an area around the first support bar 632 and through an opening in the second support surface 654 on which the subject's knees are normally positioned. The vertical shaft 610 is further attached to a horizontal shaft 614 which may function as handlebars on which the subject's hands or forearms may rest. This support for the subject's arm may help to prevent upper body movements during the operation or procedure.

The fixturing may be vertically adjustable (e.g., such as by a pin-and-pinhole mechanism 620 shown in FIG. 6). For instance, a height of the horizontal shaft 614 may be adjusted by adjusting a length of the vertical shaft 612 extending above the second support surface 654.

Other example fixtures may be supported by features of the imaging apparatus other than a seat. For example, the VersaRest™ fixture, made by Fonar Corporation, extends horizontally between sidewalls of the apparatus, instead of being supported by a vertical member. Example configurations of this and similar fixtures may be found in U.S. Pat. No. 7,239,906, the disclosure of which is hereby incorporated herein.

The examples of the present disclosure focus on imaging of a portion of the subject's back, although in other example uses of the upright MRI apparatus, a different anatomy of the subject may be imaged, such as any organ or other portion of the anatomy that is undergoing some form of medical treatment. Additionally, the examples of the present disclosure focus on a laser treatment operation; however, those skilled in the art would ready appreciate the applicability of the aforementioned technology to other minimally invasive operations for which it may be desired that a subject not move between imaging and operation. For instance, in a spinal disk decompression procedure, it may be desired to image a needle inserted into the back of a subject, while the subject is being treated.

The examples above describe imaging an anatomy of interest. However, in some instances, image acquisition may be performed for other portions of a subject's anatomy within the process of an operation. For instance, the image acquisition may include first acquiring scout scans associated with a desired portion of the subject's anatomy and thereafter acquiring higher resolution multi-slices scans of that portion of the anatomy. In addition, as the acquired MRI signals contain positional information of the portion of the imaged anatomy, those signals can be further processed by a computing device, such as to display the scanned information on a screen or monitor included in the MRI system.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system comprising:
a magnetic resonance imaging system comprising:
  a magnet;
  first and second sidewalls positioned on opposite sides of an imaging field of the magnet; and
  a seat configured to support a subject in an upright sitting position with the subject's back facing outward toward a person operating on the subject's back, wherein the magnetic resonance imaging system is capable of imaging a target anatomy of the subject while the subject is in the upright position; and
an open space configured to permit access to the person operating on the subject's back while the subject is in the upright sitting position;
a first motor for translating the seat between first and second positions, wherein the first position is within the imaging field of the magnet, such that the target anatomy of the subject is capable of being imaged while the subject is in the upright position, and wherein the second position is outside of the imaging field and in the open space, and further wherein the subject support is between the first and second sidewalls in the first position such the subject is accessible to a person only from the subject's posterior direction, and wherein the subject support is displaced from between the first and second sidewalls in the second position such the subject is accessible to persons on the subject's sides.

2. The system of claim 1, further comprising a second motor configured to rotate the seat between a first rotational position and a second rotational position, wherein the magnetic resonance imaging system is configured to image the subject in the first rotational position and wherein the subject is capable of being operated on when the subject is in the second rotational position.

3. The system of claim 2, wherein the first rotational position is an upright position and wherein the second rotational position is a recumbent position.

4. The system of claim 2, wherein the first motor and the second motor are the same motor.

5. The system of claim 1, wherein the first position and the second position are between one to four feet apart.

6. The system of claim 5, wherein the first position is within an imaging region of a magnet of the magnetic resonance imaging system, and wherein the second position is within view of an operating theatre gallery.

7. The system of claim 1, wherein the open space is within a frame of the magnet such that multiple people can operate on the subject's back from the open space.

8. The system of claim 1, wherein the seat is affixed to a bed, and wherein the seat is adapted to support the subject in the upright sitting position with the subject facing the bed.

9. The system of claim 8, wherein the seat further comprises a fixture for supporting a portion of the subject's upper body.

10. The system of claim 1, wherein the seat is configured to be mounted to a bed that is mounted to a support surface, wherein a bottom surface of the bed faces the support surface when the bed is in a partially upright or flat position, and wherein a top surface of the bed faces away from the support surface when the bed is in a partially upright or flat position, the seat comprising:
a first extension member extending upward from a first location in a direction away from a platform and away from the bed, wherein the first location is located a first distance from the bed;
a second extension member extending upward from a second location in a direction away from the platform and towards the bed, wherein the second location is located a second distance from the bed that is greater than the first distance;
a first subject receiving surface mounted to the first extension member, wherein a top surface of the first subject receiving surface faces away from the first extension member and is adapted for a subject to sit on; and
a second subject receiving surface mounted to the second extension member, wherein a top surface of the second subject receiving surface faces away from the second extension member and is adapted for the knees of the subject to rest on.

11. The system of claim 10, wherein the top surface the first subject receiving surface is angled towards the bed, and wherein the top surface of the second subject receiving surface is angled away from the bed.

12. The system of claim 10, wherein the second subject receiving surface contacts the top surface of the bed.

13. The system of claim 10, wherein at least one of the first distance or the second distance is adjustable.

14. The system of claim 10, wherein the first extension member and the second extension member intersect at an intersection point, and wherein the intersection point is adjustable.

15. The system of claim 10, wherein the second subject receiving surface includes a gap, and wherein the first extension member extends from a mounting bar to the first subject receiving surface through the gap.

16. The system of claim 10, wherein the second extension member includes a plurality of grooves, and wherein the seat further comprises a stand extending from the first extension member, the stand including:
a first end hingedly coupled to the first extension member; and
a second free end adapted to engage one or more of the plurality of grooves of the second extension member to lock the first and second subject receiving surfaces in place relative to one another.

17. The system of claim 10, further comprising:
a vertical shaft extending upward from the second subject receiving surface; and
a horizontal shaft coupled to the vertical shaft, the horizontal shaft adapted to support the subject's arms when the subject is seated on the seat.

18. The system of claim 10,
wherein the platform is mounted to the bed at a fixed point and has a length extending substantially perpendicularly from the top surface of the bed, the platform having an upper surface facing most of the bed;

a first support bar positioned on the upper surface of the platform across a width of the platform at the first location, the first extension member extending therefrom and supported by the first support bar;

a second support bar positioned on the upper surface of the platform across the width of the platform at the second location, the second extension member extending therefrom and supported by the second support bar.

19. The system of claim 18, wherein the width of the platform is substantially equal to a width of the bed, and wherein each of the first and second support bars has a length substantially equal to the width of the platform.

20. The system of claim 10, further comprising the bed.

21. The system of claim 1, further comprising: a treatment apparatus comprising a handheld treatment component adapted to be pointed at a target region of the subject in the imaging field of the magnet while the subject is supported by the seat in the upright position.

22. The system of claim 21, wherein the treatment component is one of a laser or a needle.

\* \* \* \* \*